United States Patent [19]

Lynn

[11] Patent Number: 4,568,334
[45] Date of Patent: Feb. 4, 1986

[54] INTRAVASCULAR CATHETER PREPARATION AND DISPENSING CONTAINER ASSEMBLY

[76] Inventor: Lawrence A. Lynn, Apt. 27B, 3001 S. Providence, Columbia, Mo. 65201

[21] Appl. No.: 603,685

[22] Filed: Apr. 25, 1984

[51] Int. Cl.$^4$ .............................................. A61M 5/00
[52] U.S. Cl. .................................................... 604/171
[58] Field of Search ............... 604/171, 158, 163, 164, 604/165, 166

[56] References Cited

U.S. PATENT DOCUMENTS

| | | |
|---|---|---|
| 2,937,643 | 5/1960 | Elliot . |
| 3,606,889 | 9/1971 | Arblaster . |
| 3,633,758 | 1/1972 | Morse et al. . |
| 3,648,704 | 3/1972 | Jackson . |
| 3,796,211 | 3/1974 | Kohl . |
| 3,851,649 | 12/1974 | Villari . |
| 3,894,540 | 7/1975 | Bonner, Jr. . |
| 3,926,309 | 12/1975 | Center . |
| 4,051,849 | 10/1977 | Poncy et al. ......................... 604/163 |
| 4,062,363 | 12/1977 | Bonner, Jr. ......................... 604/171 |
| 4,068,659 | 1/1978 | Moorehead .......................... 604/163 |
| 4,248,236 | 2/1981 | Linder . |
| 4,327,723 | 5/1982 | Frankhouser . |
| 4,379,506 | 4/1983 | Davidson . |

OTHER PUBLICATIONS

"Manipulation of the Pulmonary-Artery Catheter after Placement", *Anesthesiology*, 1978, 48: 373-374.

*Primary Examiner*—John D. Yasko
*Attorney, Agent, or Firm*—Rogers, Howell, Moore & Haferkamp

[57] ABSTRACT

A transparent intravascular catheter preparation and dispensing container assembly has a main housing compartment with an opening detachably covered to permit the hand to remove part of the catheter therefrom with a bumper, which can be rotatable, to prevent catheter crimping, and basin beneath a catheter port to enhance liquid visibility; and has a connector compartment housing the more proximal catheter portion which is detachably covered to allow hand removal of the catheter portion therefrom, with a slotted washer mounted between said compartments to receive the catheter; a transparent glove surrounding a more distal catheter section with pleated sections of alternating sizes; a proximal glove washer with distal funnel bore to facilitate catheter retraction and a tapered proximal exterior to facilitate taping it to the catheter after catheter insertion; a distal glove collar with a catheter guide tube mounted therein; a trough housing the glove at an upward angle, trough chambers covered by detachable lids and sized to permit the hand to grasp a glove portion to retract and remove the catheter; a test chamber with a cavity to receive the catheter distal balloon for leak testing; a tube connecting the test chamber and trough, with a catheter conduit, and a gas escape conduit extending from the test cavity top and the high point of the tube catheter conduit; an introducer tube with a recess to receive the guide tube; the catheter is initially coiled and spaced from a main housing wall to abut the wall when the catheter is retracted from the test cavity a predetermined distance to prevent further retraction, which is accomplished in one modification with the catheter coiled twice, in another modification the main housing has a bulge with the catheter initially abutting a housing wall so that when the catheter retracts a predetermined length it abuts the bulge.

95 Claims, 18 Drawing Figures

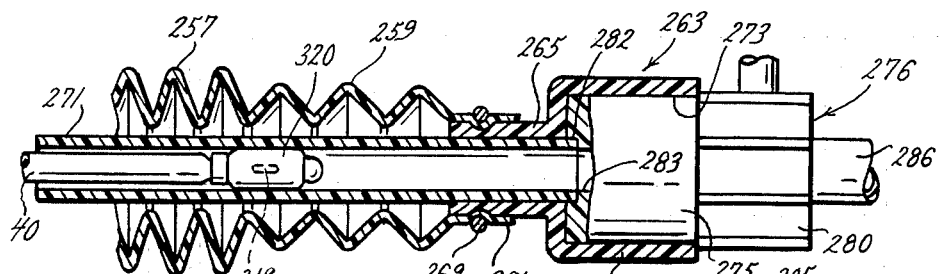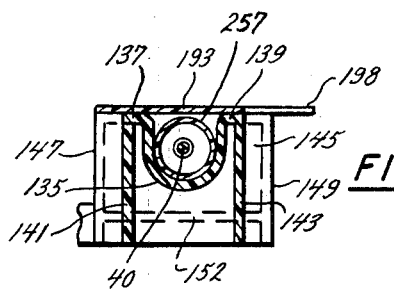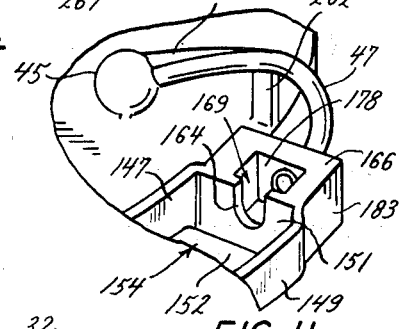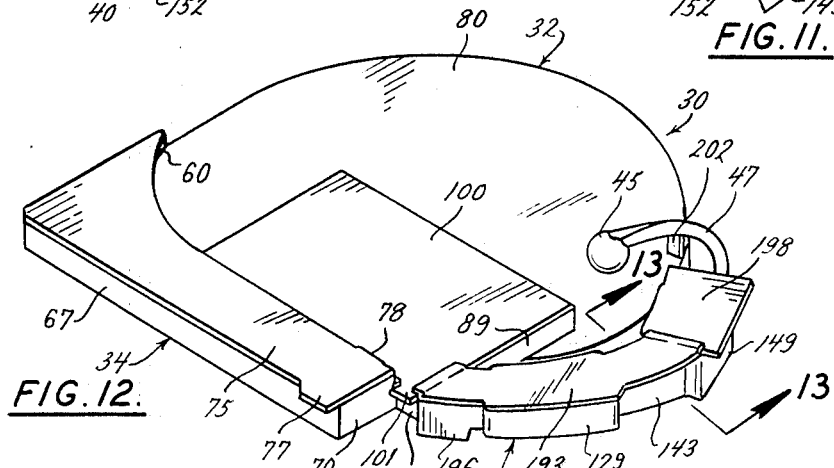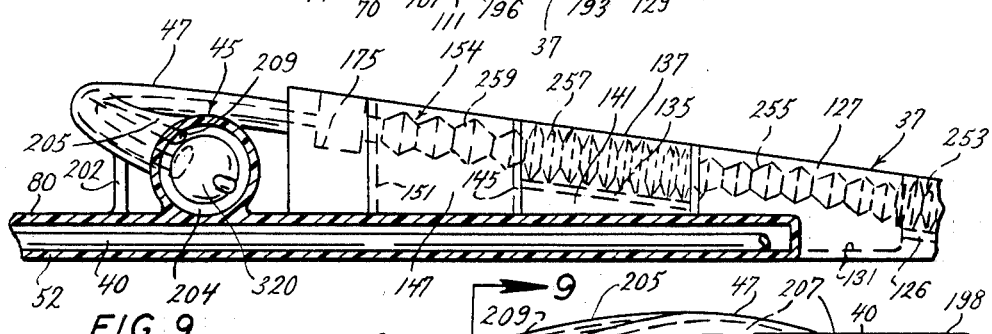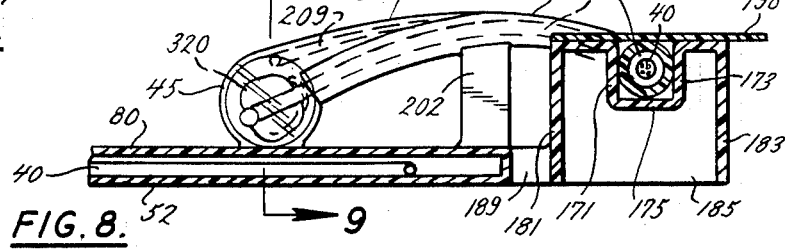

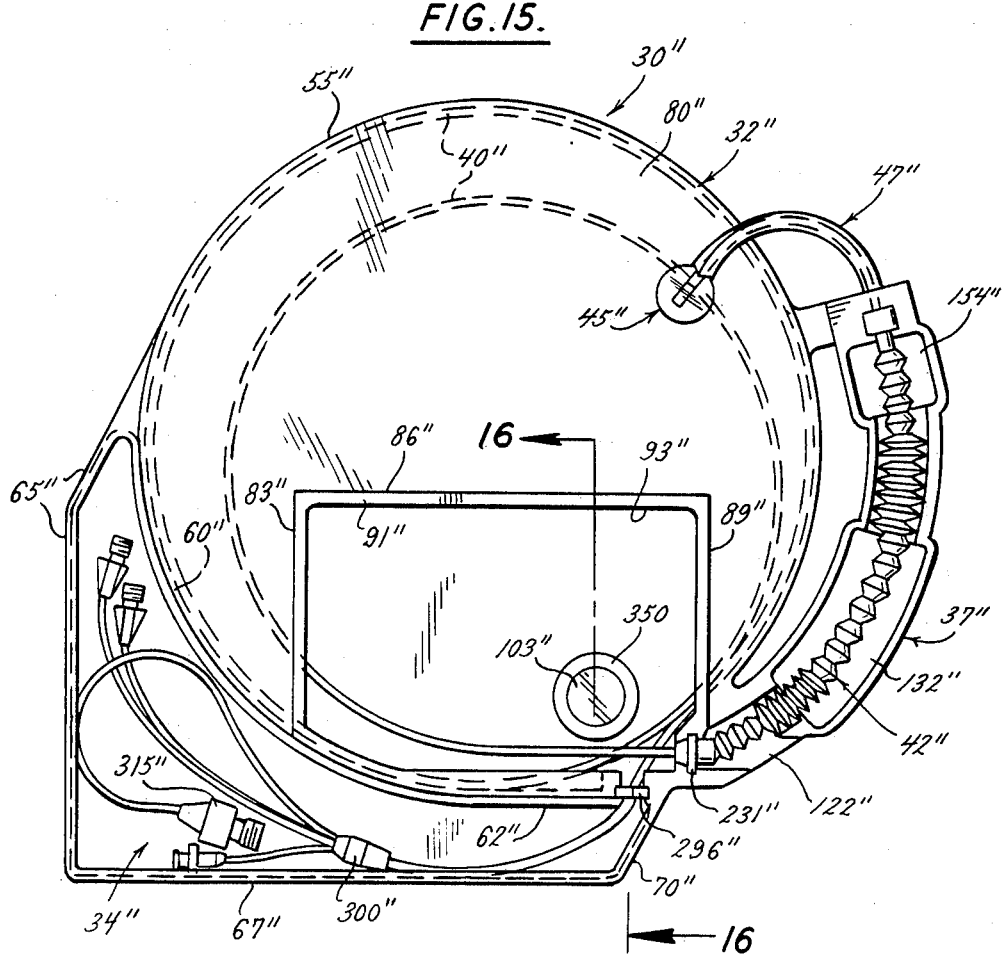

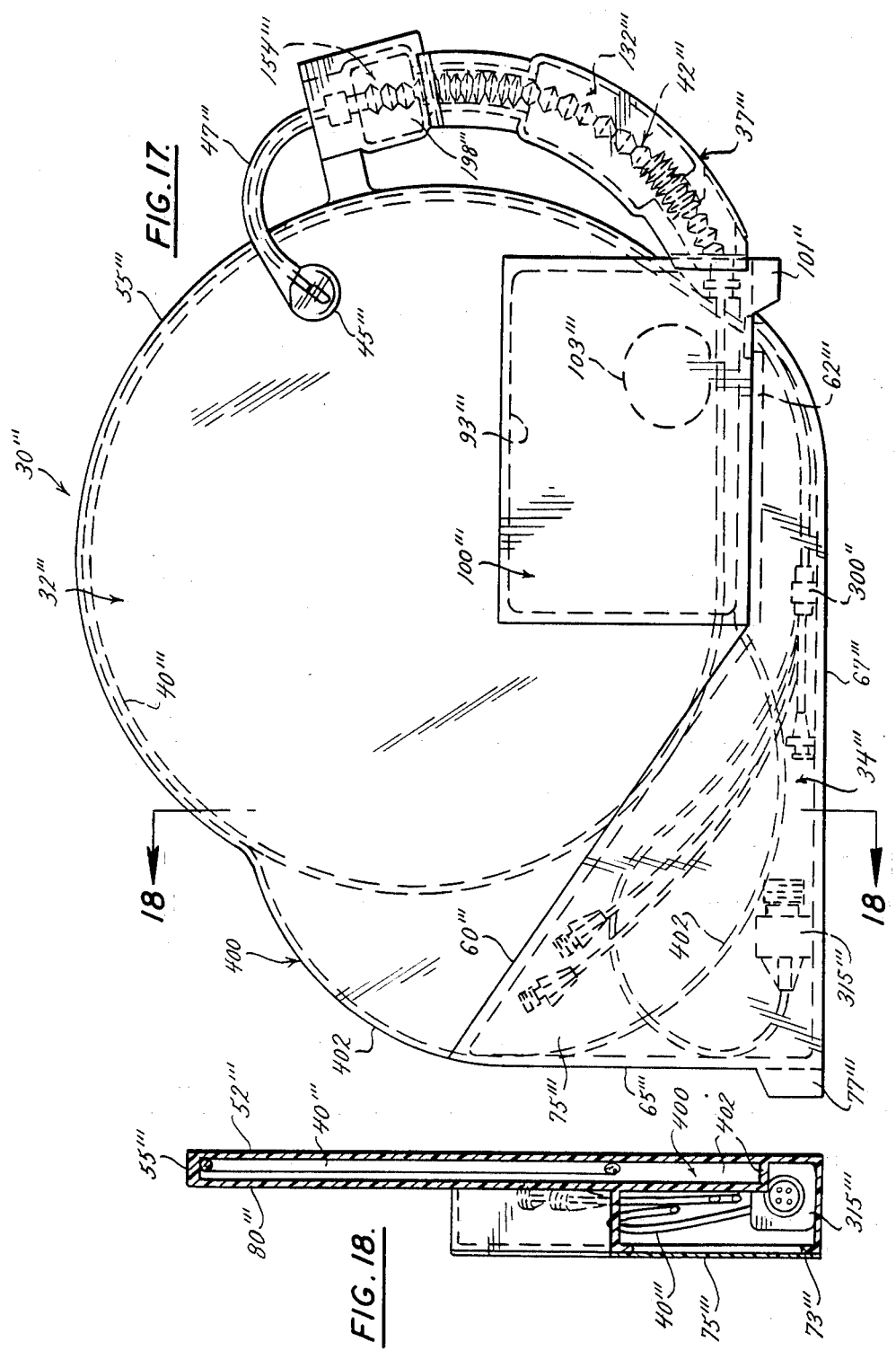

INTRAVASCULAR CATHETER PREPARATION AND DISPENSING CONTAINER ASSEMBLY

FIELD AND SUMMARY OF INVENTION

This invention relates to protective containers and covering gloves for intravascular catheters. Intravascular catheters, such as balloon flotation catheters, are inserted into the blood vessels of a patient to varying degrees, including into the heart and lungs, to allow injection of various substances into the vessels through catheter ducts, and also so that various readings, such as pressure and temperature, within the vascular system can be made by use of catheter ducts.

The insertion of such vascular catheters through the heart and into the lung requires an absolutely sterile procedure. However balloon flotation catheters are long, generally greater than 100 cm. for an adult patient, and unwieldy as well. The present art requires flotation catheters to be exposed to a potentially contaminating environment during preparation, testing and insertion of the catheter into the patient's vascular system. Operators generally wear sterile gowns, hats, masks and gloves and in addition, a large sterile field is prepared on and around the patient with multiple draping towels, all of this being done to reduce the probability of catheter contamination by contact with non-sterile objects, persons or droplet nuclei produced by the attendants.

Once the sterile field has been prepared, the catheter is disengaged from an ordinary non-compartmentalized package and the terminal for the catheter ducts are attached cautiously to their respective tubing connections.

After the connections have been made, some of the catheter ducts are flushed with a heparinized solution to avoid clot formation within the ducts and air embolism after insertion. A sterile sleeve can then be placed over the exposed catheter to provide a protective covering to be used while the catheter is indwelling after the insertion procedure.

The balloon at the distal catheter end is then placed into a bowl of sterile saline and inflated to test for air leaks. This is an important test, as insertion is potentially more dangerous if the balloon does not remain inflated. Additionally, an air leak can expose a patient to the risk of a second cardiac catheterization if a catheter with a faulty balloon is replaced. After the balloon has been tested, the catheter is inserted into a plastic sheath, called a venous introducer, which has previously been placed into a large vein, generally the subclavian or internal jugular.

The catheter is then passed into the blood vessel, the balloon is inflated with air from gas coming from a syringe which is connected to a catheter terminal in fluid connection with a catheter duct extending into the balloon, and the catheter is advanced through the vessel utilizing pressure waveform guidance through the great vessels, and also through the cardiac chambers and into the lungs where the balloon can wedge in a pulmonary artery. The balloon is then deflated and the catheter resets within the lung and rests in a more proximal portion of a pulmonary artery. The catheter is then secured, and a portion of the catheter extending from the introducer is covered by the protective sleeve, and the catheter is maintained in this in-dwelling position for a variable period of time which can extend beyond 72 hours.

During the indwelling period, the catheter can migrate to an unfavorable location. If this occurs the catheter may have to be advanced or retracted to regain an appropriate location.

The process of preparation, testing and insertion of balloon flotation catheters is associated with several problems. The procedure is often done under emergency situations, however the present art requires gowning, draping and preparation of the catheter after a large sterile field has been produced. This significantly increases the time of insertion and delays procurement of pressure, cardiac output, and mixed venous gas data which may be needed immediately to guide therapy in a patient in a life threatening situation.

Because of the length and resilient nature of an adult balloon flotation catheter, it is cumbersome to control in a limited sterile field after it is removed from a package. However the art requires considerable preparation and testing procedures to be done on the exposed catheter prior to insertion and there are many potential sources of contamination. The area surrounding the sterile field is often cluttered with non-sterile objects such as intravenous lines, respirator tubing and nasogastric section tubing. Indeed, since the sterile field must cover part of the patient, a critically ill and restless patient may move suddenly and unexpectedly to disrupt the sterile field and contaminate the catheter or operator. In addition, the operator may become unknowingly contaminated in this non-surgical environment by brushing against a non-sterile object, for example a bed sheet, while attaching the catheter to pressure tubing or during the gowning and gloving procedure. These contaminating microorganisms may then be passed from the operator to the exposed catheter or sleeve providing a nidus for proliferation of microorganisms which could potentially produce life-threatening infections within 48 to 72 hours.

It is well known that the possibility of catheter or sleeve contamination during exposed preparation and insertion as a cause of life-threatening infection is considerable. Medical literature reports problems with sleeve and catheter contamination and other related problems. For example see "Assessment of the Sterility of Long Term Cardiac Catheterization Using the Thermodilution Swan-Ganz Catheter" by Jack J. Appelfeld, Tina E. Caruthers, Donna J. Reno and Joseph M. Civetta, *Chest* Oct. 4, 1978, 74: 377–380; "Starch as a Cause of Thrombus with Swan-Ganz Catheters", Richard A. Brunswick and Thomas A. Gionis, *Chest* July 1982, 82: 131–132; "Contamination Shields for Pulmonary Artery Catheters", *Critical Care Medicine,* March 1983, p. 230; and "Manipulation of the Pulmonary-Artery Catheter After Placement", *Anesthesiology* 1978, 48: 373–374. Such problems include that sleeve and catheter culture positivity can be high after 72 hours of indwelling time (which may, in part, represent proliferation of microorganisms which contaminated the catheter or sleeve during the insertion process). Further problems include starch used on operators' hand gloves being inserted into the patient's blood system by contact of the glove with the catheter, which can lead to blood coagulation and thrombosis.

The present procedure is often performed by two operators due to the need to control the unwieldy catheter while insertion and preparation tasks are performed. This results in considerable personnel costs. Additionally, at least one operator generally must remain gowned and maintain the sterile field while awaiting X-ray confirmation should the position of the catheter be in doubt. Notably a physician may wait as long as an additional 15 to 20 minutes while awaiting the radiograph to be taken, processed and transported.

Furthermore, sterile gowns, hats, masks, a sterile bowl and a large bundle of sterile towels must be provided, which can cost the patient over $20.00. Additionally should the catheter contact a non-sterile object, or even if such contact is suspected, the catheter must be discarded at a cost exceeding $100.00. And if the operator does not recognize such non-sterile contact and the contaminated catheter is inserted into the patient, an extremely expensive and potentially fatal infection could result. (Notably, heart patients, which often require floatation catheters to assist in therapy, may be particularly intolerant of even mild infections.)

Not infrequently the catheter does not pass easily through the cardiac valves and chambers (in particular the tricuspid valve causes considerable difficulty). The catheter may have to be nearly completely withdrawn and reinserted several times before the appropriate position is achieved. To facilitate passage, an operator will often attempt to rotate the distal tip of the catheter by the application of torque to the proximal portion of the catheter. Indeed, it is often with some difficulty that the operator may coil the proximal catheter longitudinally in an attempt to apply greater torque to the distal tip during proximal rotation. Also the operator may inadvertently attempt to insert the catheter with the curved tip directed in an unfavorable direction with respect to the patient's anatomy. Such a mistake can considerably alter the course of the catheter tip as it is advanced and may result in improper position of the catheter within the patient.

SUMMARY OF THE INVENTION

The present invention acts to overcome prior art problems. The intravascular balloon flotation catheter preparation and dispensing container is divided into hermetically sealed compartments for carrying out the necessary operative steps. The compartments can be covered and hermetically sealed by detachable lids. The invention further can have a chamber which can act as a trough within which a portion of the catheter extends, which trough in the preferred embodiment is connected to the container. The catheter within the trough can be surrounded by a pleated tubular glove having alternating larger and smaller pleated segments which permit adequate compression and expansion of the glove for long unimpeded thrust in either direction when the catheter is being inserted or extracted from the blood vessel of a patient. The glove is resilient to rebound to its original position when released by the operator during the insertion or retraction process.

In the preferred embodiment the glove provides the characteristic of elastic expansion of large pleats with near nonelastic compression of smaller pleats (or potential pleats). This novel characteristic provides a mechanism whereby larger trailing expansion pleats rebound the glove after each insertion or retraction thrust. This mechanism allows smooth insertion or retraction without requiring the glove to have significant tubular rigidity therefore producing finger to glove to catheter sensitivity and catheter flexibility during insertion similar to that associated with gloved hand insertion. The nonelastic compressibility of the smaller pleats (or potential pleats) further allows a stable compression of the glove to be maintained should a stable, more advanced position be required after the catheter has been indwelling and previously secured to a funnel washer by tape.

The trough is of such configuration that the operator's fingers and thumb can be inserted into it to grasp the glove. The trough can have compartments which are covered by transparent lids, which hermetically seal the trough and the glove and catheter within it.

The glove has its ends secured to structure surrounding the catheter so that the inside volume within the glove can be maintained in a sterile atmosphere.

A test chamber can be provided, and can be connected with the container, to receive the distal catheter end having the flotation balloon. During operation, the balloon can be inflated within the chamber and tested for leaks in a completely sterile environment.

In a preferred embodiment, the container has a catheter connector compartment which houses the proximal end of the catheter and the various inlet tubes which pigtail out from it and are in fluid connection with the catheter ducts, as well as housing the terminals for those inlet tubes which can include a thermistor, the gas inlet tube terminal, and terminals for fluid flow. This compartment can be separated from the rest of the container by walls.

The connector compartment is covered and hermetically sealed by a detachable lid which can be peeled away by the operator's hand to expose the proximal end of the catheter and the various terminals and inlet tubes so that the operator can grasp them and lift them out of the compartment.

A second main housing compartment houses a larger coiled portion of the catheter. The walls of this compartment are preferably such that when the catheter is withdrawn into it during removal of the catheter from the test chamber the catheter abuts the wall to prevent removal of the distal catheter end from a catheter guide tube mounted to the distal glove end. This main compartment has an opening through its roof which can be covered by a lid hermetically sealing it from the exterior environment. The lid can be peeled away by the hand during operation for removal of the catheter through the opening.

In a preferred embodiment, the proximal end of the trough is integral with the structure within which the catheter is coiled, and the catheter lies within the trough. The trough is slanted upwardly to gradually elevate the catheter as it extends towards the test chamber.

The pleated catheter glove lies supported within the trough to surround a portion of the catheter. The glove can be attached at its distal end to a collar. A catheter guide tube is mounted within the collar and extends into the glove and also forwardly into the head area of the collar. The catheter, in its initial position in the container, extends through the guide tube. As the catheter is withdrawn from the test chamber, it is removed to a point so that it still lies within the catheter guide with its distal end is within the glove. This prevents the distal catheter tip from swinging about loosely within the pleated glove section which could create difficulties in moving the catheter back into the collar.

When the distal section of the catheter is removed from the container, a novel introducer is attached within the collar. The introducer has a recessed area to receive the distal tip of the guide tube, with the bore of the guide tube in alignment with the bore of the introducer.

The trough has at least one operator grasping section sized to permit the operator to extend his fingers and thumb into the trough to preferably reach underneath the glove to pull it upward and outward from the trough. In the preferred embodiment, there are two such grasping sections. In the preferred structure, the trough also has a recessed area to receive the collar at the distal end of the sheath.

The test chamber in the preferred embodiment is mounted to the container above the coiled catheter. A tube has one end connected to the distal trough end and its other end connected to the test chamber to have its principal tube conduit in fluid communication therewith so that the catheter can pass from the trough through the tube and into the test chamber. The tube has a second conduit for gas escape from the test chamber cavity which extends from the top of the test cavity to the highest point of the tube, at which point it opens into the tube catheter conduit. The gas escape conduit permits gas initially within the test chamber cavity to escape therethrough when the test cavity is later filled with saline solution for testing, and also permits gas from the test cavity which may emerge during balloon testing to escape therethrough.

In a preferred embodiment, the trough has two separate detachable lids. The proximal lid extends from the proximal trough end to cover at least one of the operator grasping chambers, and can be peeled away to expose that chamber. The distal lid extends over the second operator grasping chamber and over the recess for the glove collar, and can be peeled away to expose that chamber and recess. The trough furthermore has a passageway near its proximal end through which the glove can be laid after it has been lifted out of the trough, so that the collar can be attached to the introducer, and the catheter inserted into the blood vessel of a patient.

The trough has near its proximal end a washer through which the catheter passes. This washer can have an interior funnel shape to facilitate the retraction of the catheter through it into the main housing of the container. The proximal end of the glove can be secured about the exterior of this washer and the washer can extend through a mount plate removably mounted to the container, and the mount plate can also have a downward extending slit for ease of assembly and disassembly. The washer can also have a tapered proximal end to facilitate application of tape to it and to the catheter to hold the catheter in relative fixed position once the catheter has been inserted to the desired point in the patient's body after the washer has been detached from the container.

Another washer can be provided in the wall of the catheter connector chamber to allow passage of the catheter into the main housing compartment. This washer can have an upwardly extending slit to permit the catheter to be pulled therethrough when the proximal catheter portion is removed from the catheter connector compartment. Alternatively the entire washer can be removably mounted and can be disconnected from the container.

The preferred embodiment also has a bumper within the main housing compartment which preferably is near the proximal trough end. The bumper can be round, and acts to resist crimping of the catheter when the catheter coil size is reduced as the catheter is withdrawn from the container into the patient. In a modification, the bumper can be a rotatable tube mounted to a fixed member, to rotate freely with movement of the catheter about it. The preferred embodiment additionally has a small basin in the floor of the container below the location of one of the catheter ports when the catheter is in its original position. The basin facilitates viewing the emergence of saline solution through that catheter port.

In the preferred structure the various lids can have portions which are gas permeable but bacteria impermeable to permit gas sterilization within the various container parts, and can also be transparent. The walls of the container are preferably of transparent plastic so that the operator can view the position of the catheter at all of its various points including within the test chamber, the tube leading to the test chamber, the trough, the catheter connector compartment, and the main housing compartment. The glove is likewise preferably of transparent material so that the catheter can be viewed therein. The entire container can be within a flexible transparent hermetically sealed package.

In one modification, the main housing compartment has an adjacent bulging section, and the catheter initially abuts the walls of the main housing compartment. When the catheter is withdrawn from the test chamber, the catheter is pushed into the bulging section. This modification has the advantage of having the catheter in a stable condition abutting the wall while the container is being shipped and handled.

In another modification, the catheter is coiled twice within the main housing, so that the main housing, and the entire container, are of more compact size and can more easily accommodate a catheter of longer length. The outer coil can abut a wall of the main housing, and the smaller inner coil can expand in size to also abut the main housing wall when the catheter is withdrawn the desired amount into the main housing. The bumper for this modification can have a rotatable tube to freely rotate as the catheter contracts about it, thus facilitating insertion of the catheter.

The invention provides many advantages over the prior art. The container provides a sterile enclosure for the catheter within. After removing the container from the package, the operator initially removes by his hand the lid over the catheter connector compartment to expose that compartment. The operator's thumb and fingers (phalanges) can reach into the connector compartment to grasp the various terminals of the inlet tubes for the catheter so that they can be connected. With a typical catheter two of the terminals will be connected to saline solution sources for flushing of the catheter ducts connected to those terminals. One of these ducts extends to a port in the distal tip of the catheter, and the solution fills the test chamber cavity. The other duct extends to a more proximal port positioned above the container floor basin so that when it is irrigated, the solution can be viewed pouring into the basin. The terminal for the gas duct can be connected to a syringe and injected with gas so that the balloon housed within the test chamber cavity is inflated and can be viewed for the emergence of gas leak bubbles. If no gas leaks are found, the balloon can be deflated. The thermistor terminal can likewise be connected so that proper temperature readings from the catheter can be obtained.

Then the lid over the more proximal area of the trough can be removed by the hand to expose at least one of the operator grasping chambers, and also to expose the exit passageway for the glove. The operator's thumb and fingers (phalanges) can grasp the glove within the trough and with a series of gentle retraction thrusts, withdraw the catheter from the test chamber and slightly into the glove area so that the distal catheter end still remains within the catheter guide tube. The thrusts are such that once the retraction thrust is completed, the glove is released so that the resiliency of the glove pleats, after expansion, rebounds the glove back to its original position to allow the process to be repeated.

Next, the other trough lid can be removed by hand to expose the other operator grasping chamber and the glove collar. The entire container is then placed with the trough passageway positioned opposite the introducer which has been previously inserted within the patient, with the direction of the potential distal catheter curve directed favorably with respect to the patient's vascular system. Then the glove is grasped by the operator's hand and moved out of the trough and then moved so that the glove extends through the trough passageway. Next the glove collar is connected to the introducer, and the catheter is gradually advanced through the introducer into the patient's blood vessel.

The balloon can be inflated as is known in the art, and the various steps necessary to catheter insertion within the patient can be performed. After determination is made that the catheter is in the correct position in the patient's vascular system, such as in the heart or lung, the lid covering the opening in the main housing chamber can be removed by the operator's hand to expose that opening, and the operator's hand can reach therethrough and grasp the catheter and remove it from the container. When this occurs, the first washer near the proximal trough is pulled away from the container, and also the catheter is pulled through the slit in the second washer near the catheter connector chamber to be removed therefrom. The first washer can then have its tapered end taped to the catheter as described previously.

The invention thus provides a compact sterile enclosure advantageous for storage and transport of a balloon flotation catheter in a coiled position and provides a sensible and easily learned step wise approach to sterile preparation, testing, insertion, withdrawal and maintenance of a balloon flotation catheter. A catheter shape is maintained which is favorable for inserting the catheter while minimizing the opportunity of inadvertent misdirection of the catheter tip during insertion.

The providing of the various compartments allows the operator to work with the catheter components of that compartment without exposing other portions of the container to a non-sterile environment. For example while work is being done with the catheter within the catheter connector compartment, the rest of the catheter is protected, and likewise as work is being done on the first or second exposed trough chamber, the main housing protects against exposure to a non-sterile environment.

The test chamber permits inflation and testing of the balloon without having to move the catheter and the balloon from one point to another relative to the container, and thus reduces necessary movement for an operator and further provides a sterile protected environment for testing while maintaining other portions of the catheter housed within protective compartments.

The invention further allows the catheter to be inserted within the patient's body, and for tests to be performed concerning the proper position of the catheter while the catheter is still housed within the sterile environment of the main housing compartment. The device further allows for the unattended maintenance of catheter sterility over a period of hours without physician handling during X-ray confirmation of catheter position, and yet allows for the sterile withdrawal and reinsertion of a large portion of the catheter length should the position be found unsatisfactory.

The invention further allows for the catheter to be inserted without the operator having to touch the catheter directly by virtue of use of the novel pleated glove so that not only are contaminating microorganisms prevented from entering, but also other substances such as starch which might be placed on gloves fitted to the operator's hands, prevented from entering the patient's system to thus reduce chances of a thrombus or other vascular complication.

In addition, the housing of the coiled catheter within the container allows for the operator to magnify torque to the catheter by rotating the container itself to turn the catheter within the patient's body to maintain a better angle for entrance into a particular vascular area, so that the operator need not grasp the small catheter and try to rotate it to obtain such torque.

The invention thus reduces the need for expensive sterile gowns, hats, masks, bowls and large packages of sterile drapes while reducing personnel expenses by allowing for the preparation and testing of the catheter prior to insertion. The invention further reduces the necessity of discarding and wasting catheters which become contaminated under the present state of the art, and further reduce the probability of a patient becoming infected by a contaminated catheter, or having some other substance, such as starch, inserted within the body which could cause vascular complications. The time for insertion is greatly reduced which can be critical under the emergency circumstances with which such insertion is frequently accompanied. The various steps can be performed with minimal movement of the operator and catheter to thus reduce the likelihood of bumping or otherwise touching the catheter to contaminating substance or material which should not be within the vascular system.

DESCRIPTION OF THE DRAWINGS

FIG. 8 is a section taken on the line 8—8 of FIG. 1;

FIG. 9 is a section taken on the line 9—9 of FIG. 8;

FIG. 10 is a section taken on the line 10—10 of FIG. 1 showing the catheter tip within the guide tube and within the distal end of the glove, with the glove collar removed from the container and connected to an introducer;

FIG. 11 is an orthogonal projection of the distal end of the trough, and of the test chamber and connecting tube;

FIG. 12 is a orthogonal projection of the container removed from the package before any of the lids have been removed;

FIG. 13 is a section of the trough taken on the line 13—13 of FIG. 12;

FIG. 14 is an orthogonal projection of the lower righthand portion of the container structure as viewed from FIG. 1, with the lids, the washers, the catheter and glove removed;

FIG. 15 is a top plan view of a modification of the container showing the catheter coiled twice within the main housing chamber;

FIG. 16 is a section taken on the line 16—16 of FIG. 15;

FIG. 17 is a top plan view of another modification of the invention in which the container has a bulging section to receive the catheter as it is withdrawn, and in which a portion of the coiled catheter is initially abutting a section of the curved container wall; and FIG. 18 is a section taken on the line 18—18 of FIG. 1.

DESCRIPTION OF PREFERRED EMBODIMENT

Figure 1:
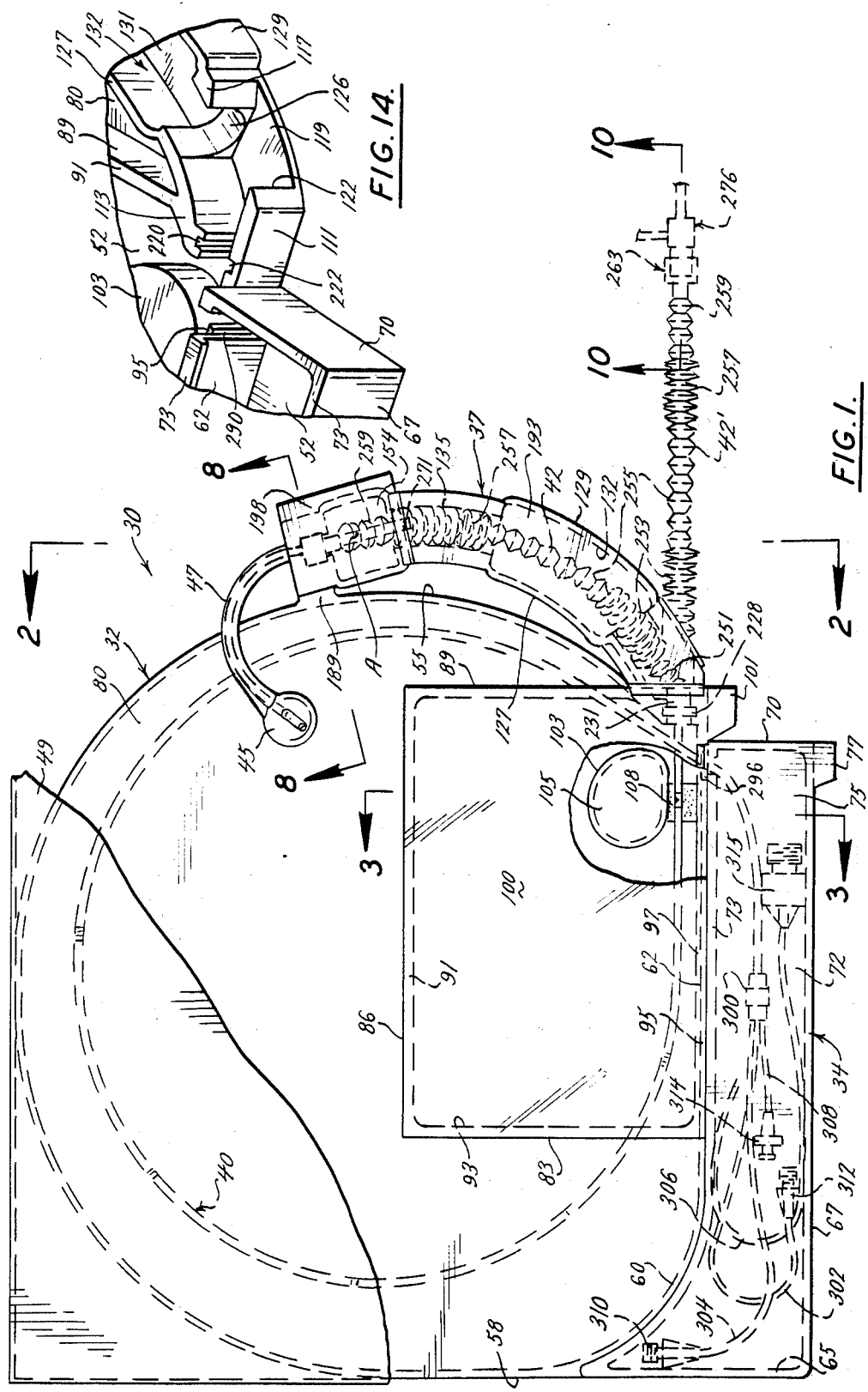
FIG. 1 is a top plan view of the container and its package, with some parts shown broken, and with the glove and introducer also shown in a second horizontal operating position extending through the trough passageway.
Figure 2:
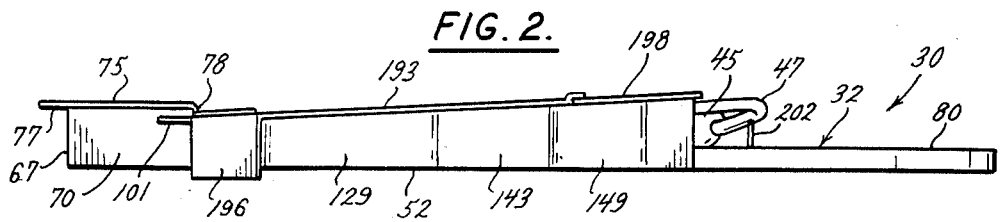
FIG. 2 is a plan view of the container removed from the package, taken from the right side of FIG. 1.

With reference to FIGS. 1-14 of the drawings, the intravascular balloon flotation catheter preparation and dispensing container is shown generally as 30. At this point we note some of the components comprising the main housing compartment 32, catheter connector compartment 34, support trough 37, vascular-catheter 40 housed within the container 30, pleated glove 42 which surrounds a portion of the catheter 40 and is housed within the trough 37, balloon test chamber 45 and the curved tube 47 connecting the test chamber 45 to the trough 37, and also reference is made to a flexible transparent plastic outer enclosing package 49 within which the container 30 can be initially hermetically enclosed.

Figure 3:
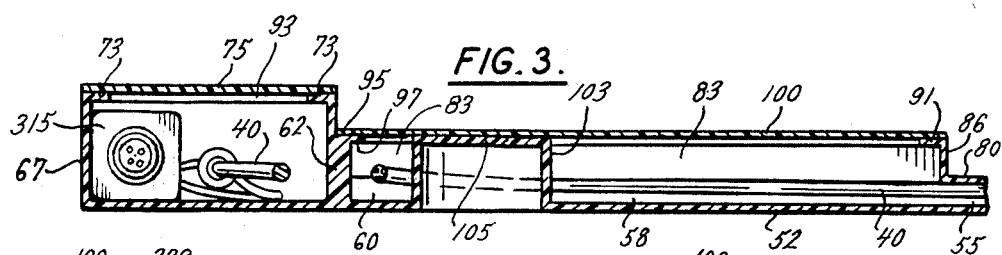
FIG. 3 is a section taken on the line 3—3 of FIG. 1.
Figure 5:
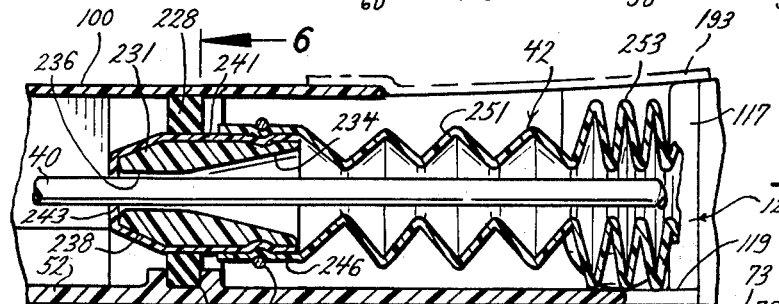
FIG. 5 is a section taken on the line 5—5 of FIG. 4 showing the washer at the proximal end of the glove.
Figures 6, 7:
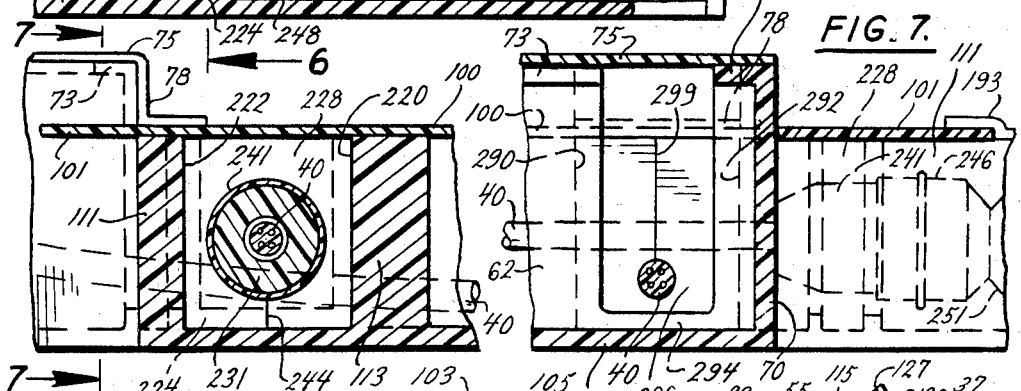
FIG. 6 is a section taken on the line 6—6 of FIG. 5.
FIG. 7 is a section taken on the line 7—7 of FIG. 6.

The container 30 has a flat floor 52 as seen primarily in FIGS. 3, 8 and 9, and also in FIGS. 5, 6 and 7. Extending upwardly from the rear and right side (right as viewed in FIG. 1) of floor 52 is a curved wall 55, which is of generally a three-fourths circular shape and which at the left end straightens out into a tangential segment 58 and thence curves forwardly and inwardly to fork in one direction into a segment 60 which then extends into another straight segment 62, with wall segments 60 and 62 being taller than wall sections 58 and 55.

The other fork branching off from wall segment 58 extends into a straight segment 65 which right angles continuously into a straight segment 67 which thence right angles into a segment 70 so that the five wall segments 60, 62, 65, 67 and 70 all of which are the same height, enclose the catheter connector compartment 34. An integral lip 73 protrudes inwardly and continuously from the tops of all the wall segments 60, 62, 65, 67 and 70, so that a flexible plastic and/or gas permeable paper lid 75 has its outer edges attached by adhesive to lip 73 to cover and seal the top of compartment 72. The lid 75 has an integral tab 77 which can be grasped with the thumb and forefinger and pulled upward and inward to peel the lid 75 from lip 73. Lid 75 has a depending flap 78 on the side opposite tab 77 which covers an exit area in wall 62 to be described.

A flat plastic roof 80 extends inwardly from the tops of walls 55, 58 and 60 above the main housing compartment 32. Extending integrally upward from roof 80 are three walls 83, 86, and 89 which along with the wall 62 form a rectangle having an opening 93 formed within said walls for subsequent catheter 40 removal. The walls 83, 86 and 89 have an integral lip 91 extending inwardly and continuously from the tops thereof. Wall 62 is slightly indented at 95 on its rear side and has a lip 97 of the same height as lip 91 extending flush from indentation 95. A lid 100 of flexible plastic which may be gas permeable or which can also have a paper area which is permeable to gas but impermeable to bacteria, has its outer edges continuously secured upon lips 91 and 97 by adhesive to seal opening 93.

Tab 101 is integral with lid 100 and can be grasped with thumb and fingers and pulled towards the opening 93 to peel lid 100 from the lips 91 and 97 to thus expose the opening 93.

From the bottom of floor 52 rises an integral bumper 103 of generally cylindrical shape with a flat top 105 which is flush with the bottom of lid 100. Integral with floor 52, between the bumper 103 and wall 62 is a small basin 108 for catching fluid pouring out of a port in catheter 40 during irrigation of that port to enhance visibility of that fluid.

Figure 4:
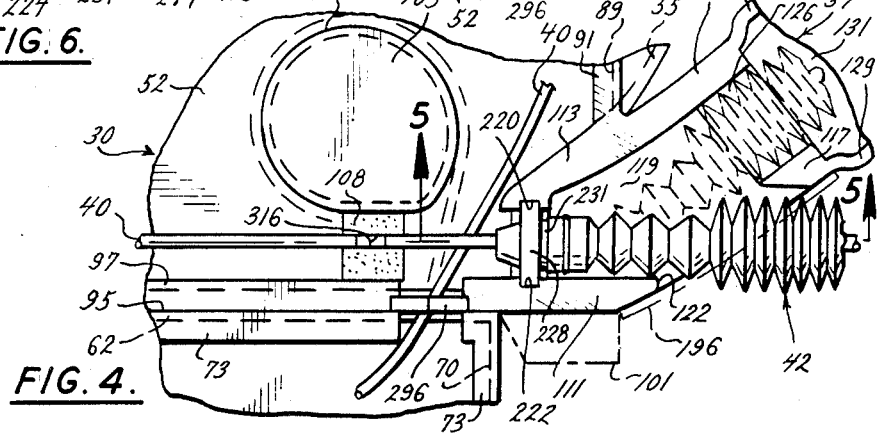
FIG. 4 is a top plan view of a portion of the container in the right corner portion of FIG. 1

Turning now to the structure of the trough 37, as seen more clearly in FIG. 4, in the lower right corner of the container 30 the trough 37 has a proximal wall 111, which is aligned with wall 62 but thicker than wall 62, and an angled proximal wall 113 which integrally junctures with the thinner walls 55 and 89. A trough wall section 115 extends integrally from wall section 113 and also from walls 55 and 89. On the opposite trough side from wall 115 is a short wall section 117, with a flat floor 119 solidly connecting the lower edges of walls 111, 113, 115 and 117. A passageway 122 is formed between the outer end of wall 111 and wall 117 for receiving the sheath 42 during removal of the catheter 40 from the container 30. Between wall 117 and a section of wall 115 of corresponding size is an integral "U" shaped floor 126.

Branching distally from trough walls 115 and 117 are thinner integral walls 127 and 129, respectively, which are at their bottoms integrally connected by a flat floor 131 to form an operator grasping chamber 132 of sufficient width to allow the thumb and fingers to be inserted therein to grasp the portion of glove 42 contained therein, and with the floor 131 spaced sufficiently beneath glove 42 to allow the thumb and fingers to be place somewhat on the underside of the glove 42.

Trough walls 127 and 129 thence extend distally into a more narrow U-shaped support section 135 as seen in FIG. 13 with the upper edges of U-section 135 branching out at the top into flanges 137 and 139 and thence extending downwardly into legs 141 and 143.

Next, U-section 135 extends distally and into an integral flat end wall 145 which at its outer edges extend distally into two integral side walls 147 and 149, which extend integrally into a perpendicular rear wall 151, with a flat floor 152 integrally connecting the lower edges of walls 145, 147, 149 and 151 so that said walls and floor form a second operator grasping chamber 154. As with floor 135, floor 152 is down a sufficient distance to allow the thumb and fingers to be inserted within chamber 154 and placed somewhat beneath the underside of the glove 42 contained therein to allow lifting the glove 42 upwardly.

Wall 151 has a U-slot 164 therein, and a flat ceiling wall 166 extends from the top of wall 151 and has a rectangular recess 169 formed therein by two side walls 171 and 173, a floor 175, (FIG. 8.) and a distal wall 178 for housing an introducer collar to be described.

Extending downwardly from the edges of ceiling 166 are integral supporting leg walls, 181, 183, and 185. Walls 178 and 185 both have aligned circular bores therethrough to telescopically receive the end of tube 47 and to be secured thereto by adhesive.

As seen in FIGS. 1 and 8 in particular, leg wall 181 and receptacle wall 55 are connected by a buttress 189 to stabilize trough 37. As seen in FIG. 9, the trough floors 126, 135 and 175 are slanted upwardly to facilitate utilization of the test chamber 45.

Trough 37 has two separate lids, the proximal lid 193, which may be comprised of gas permeable paper and/or plastic, has its side edges secured by adhesive to the tops of the distal end of wall 111, to the tops of walls 115, 117, 127 and 129, and to the U-section flanges 137 and 139. Lid 193 has a depending proximal side tab 196 secured by adhesive to the exterior of walls 111 and 117 and to the edge of floor 119 to form a secure seal about passage 122, with the lower part of tab 196 extending beneath floor 119 for grasping by the thumb and fingers. The proximal end of lid 193 extends inwardly towards the container 30 a slight distance so that it covers a portion of lid 100 to provide a secure seal at the juncture of those two lids. The tab 196 can be grasped by the thumb and fingers to peel it away from the trough 37 and expose the trough volume beneath it including chamber 132 and U-section 135.

The trough's distal lid 198 is, as shown in FIGS. 1, 8 and 12, can be composed of gas permeable paper and/or plastic and can be transparent, and is of a generally rectangular shape with adhesive on its underside securely attaching it to the ceiling wall 166 at the distal end of the trough 37, and to the top of walls 145, 147, 149 and 151 thus seal grasping chamber 154 and introducer recess 169. The interface of lids 193 and 198 is such that the distal end of lid 193 extends slightly upon the proximal end of lid 198 to be sealed securely thereto by adhesive. Referring to FIGS. 1 and 8, the lid 198 projects outwardly from walls 183 and 185 so that after lid 193 is peeled away, lid 198 can be grasped by the thumb and fingers and pulled to peel it away to expose recess 169 and chamber 154.

Turning now to the structure of test chamber 45 and tube 47, a support column 202 has its upper end adhesively secured to the underside of curved tube 47, and its lower end adhesively secured to receptacle roof 80. The spherical test chamber 45 has its underside glued or otherwise attached to a conforming curved recess in the top of wall 80 as seen in FIG. 8, and chamber 45 is hollow to contain a spherical cavity 204 within. Tube 47 flares outwardly at its distal end into a larger section 205, and a main conduit 207 extends the entire length of tube 47 for purposes of allowing passage of catheter 40. A second gas escape conduit 209 is illustrated as extending from the end of enlarged tube section 205 for about one-third of the tube's length to the highest point of the arch of tube 47 at which point it opens into main tube conduit 207. Test chamber 45 has a bore of conforming shape with the enlarged tube end 205 to telescopically receive same and be secured thereto by an adhesive so that the test cavity 204 is in communication with tube conduits 207 and 209. Tube 47 and its conduit 207 arch to a point such that a portion of conduit 207 is entirely above the highest portion of the test cavity 204 to prevent leaking. Alternatively conduits 207 and 209 can be unified into one conduit which would enter the top of the test chamber.

Turning now to the mounting of the glove 42, at the lower right corner of container 30, as seen more clearly in FIGS. 4, 5, 6, and 14, walls 111 and 113 have recessed slots 220 and 222 co-extending with a lower slot 224 formed between two ribs protruding upwardly from floor 52 (FIG. 5). A rectangular mount plate 228 has its outer edges telescopically received within slots 220, 222 and 224 to permit plate 228 to be slid upwardly and removed therefrom. Mount plate 228 has a cylindrical bore to receive a funnel washer 231 of rubber or plastic which may be flexible or somewhat rigid, washer 231 having a funnel bore 234 which tapers into a cylindrical bore 236 both of which permit catheter 40 to extend therethrough. The proximal end of funnel washer 231 is externally tapered at 238 for purposes of taping washer 231 to the cather 40 after insertion is complete.

An elastic plastic or rubber casing 241 wraps about washer 231 and extends inwardly into a circular proximal end 243 having a cylindrical bore whose edge clutches against the exterior of catheter 40 to provide stability and resist nonvolitional longitudinal catheter movement and also to provide a circumferential seal about the catheter 40. As seen in FIG. 5, the outer surface of casing 241 fits snugly against the cylindrical bore in mount plate 228 so that the casing 241 and washer 231 are snugly mounted therein, and if desired adhesive can provide additional securing of plate 228 to casing 241, or washer 231 can have a circumferential groove to receive the edge of the mount plate bore. Mount plate 228 can also have a self-sealing slit 244 in its interior aspect between cylindrical bore and floor 52 to allow easy assembly during manufacture.

At the distal end of casing 241, the proximal end 246 of glove 42 is snugly secured thereabout by a flexible "O" ring 248 which presses casing 241 into a small circumferential indentation extending about washer 231. In addition adhesive can be used to provide greater security of contact areas of glove 42 and casing 241 and funnel washer 231.

Glove 42 thence extends into a first pleated section 251, and thence extends into a second pleated section 253 having pleats of larger size than those of section 251, and next extends into a third pleated section 255 of smaller pleats than those of section 253, and thence goes into a section 257 of larger pleats, and finally into a section 259 of smaller pleats. All of the glove pleated sections 251, 253, 255, 257 and 259 can be of transparent resilient plastic so that the operator can view catheter 40 therein. The glove 42 is thus divided into alternating sections of greater resilience and lesser resilience, with the greater resilience being with the sections 253 and 257 of larger pleats, and the lesser resilience being with the sections 251 and 255 of smaller pleats. The smaller sections 251 and 255 can also be nonpleated and nonresilient, or very weakly resilient.

As seen in FIG. 10 in particular, pleat section 259 extends into a glove distal end 261. An introducer collar 263 has a cylindrical neck 265 extending integrally into a head 267, so that glove end 261 can have an "O" ring 269 circumferentially extending thereabout to press a portion of glove end 261 into a circumferential indentation about neck 265 to snugly secure the glove end 261 thereto. Adhesive can be added to additionally secure this contact between glove end 261 and neck 265.

A cylindrical tubular catheter guide 271 has its distal end telescopically received securely within the cylindrical bore of neck 265 with the distal tip of guide 271 projecting slightly into the cylindrical bore 273 of head 267.

Description will also now be made of the components to which the head 267 and guide 271 are connected when they are removed from trough 37 during operation. When this connection is made, head bore 273 has mounted within it the plastic cylindrical end 275 of a venous introducer 276, which may have a circumferential groove to receive an "O" ring (not shown) to retain introducer end 275 therein. End 275 extends proximally into a section 280, and end 275 has a short cylindrical bore 282 to snugly receive the distal end of guide 271, which extends into a bore 283 of the same diameter as the bore in guide 271. Bore 283 has a valve mechanism (not shown) known in the art and is aligned with tube 271 and extends into an introducer bore (not shown) which telescopically receives the cylindrical end of an insertion tube 286 which is known in the art, and which is put in connection with a vein or artery of the patient. The introducer collar 263 may interface with other introducer, or introducer cap with sideport, designs as are known in the art.

Focusing now on the catheter connector compartment 34 and its abutment to the area near the bumper 103, compartment wall 62 has, as seen in FIGS. 4, 7 and 14, side slots 290 and 292 in the portion of wall 62 beneath lip 97 and a bottom slot 294 rising up from floor 52, which slots receive a rectangular flexible rubber or plastic washer 296 having a circular bore in its lower portion to snugly fit around catheter 40, which is shown with a vertical self-sealing slit 299 extending upwardly therefrom to the washer 296 top so that after the overlying structure is removed, the catheter 40 can be pulled through the slit 299 to disengage it from washer 296, or the washer 296 can be disengaged from the catheter 40 after they have been disengaged in toto from container 30.

Lid 100 extends above slots 290 and 292 to cover the opening formed thereabove. The depending flap 78 of lid 75 has its edges secured by adhesive to the wall 62 on the sides of the opening in it formed above slots 290 and 292, with the lower edge of flap 78 overlapping upon the top of lid 100 and secured thereto by adhesive to seal compartment 34. Alternatively connection compartment 34 may be modified such that walls 65 and 70 slope downward from wall 67 until they are equal in height to walls 83, 86, and 89, as will be further discussed in the description of the modification of FIG. 15.

The balloon flotation catheter 40 is one known in the art, such as the Swan-Ganz catheter. At its proximal end it has a pigtial 300 which receives four tubular inlet tubes 302, 304, 306 and 308 each of which is connected as known in the art within pigtail sheath 300 to four ports for four ducts which extend through the catheter, such as seen in the cross-sectional catheter views of FIGS. 6 and 7, to various outlet ports. More inlets and catheter ducts can be provided as is known in the art. Looking now at the overall extension of catheter 40, as illustrated in FIG. 1, from pigtail 300 catheter 40 extends through washer 296 as aforesaid into the main receptacle compartment 32 and circles threreabout to pass between bumper 103 and wall section 62, and thence extends through the funnel washer 231 through glove 42, through catheter guide 271, through introducer collar 263, through curved tube 47 and into test chamber 45.

Inlet tubes 302 and 304 terminate into threaded tubular connector terminals 310 and 312, respectively. Outlet tube 308 is for connection to a gas supply source for expanding a balloon to be described, and connects into a terminal connector 314 having a valve as is known in the art. Tube 306 is connected to a threaded thermistor terminal 315 known in the art. The catheter duct connected to inlet tub 304 terminates at a port at the distal tip of catheter 40, while the catheter duct connected to inlet tube 302 terminates at a port located on point 316 on catheter 40 which is in the storage position located above the floor basin 108, as seen in FIG. 4, which is approximately 30 cm from the distal catheter tip.

The catheter duct connected to thermister 315 and its inlet tube 306 has a port located about 3.75 cm from the distal tip with proper material within the conduit to provide the thermister to function.

The catheter duct connected to gas inlet 314 extends to catheter outlet port 318 (FIG. 10), with a flotation balloon 320 hermetically secured to catheter 40 on both sides thereof, as known in the art, to allow gas from gas inlet 314 to flow through port 318 to expand balloon 320.

With respect to the entire container 30, the provisions made for gas permeability are such that the device can be sterilized throughout by gas exposure.

The various container and compartment walls described, the trough 37, and bumper 103 can all be integrally molded as one structure if desired, and can be transparent plastic. The tube 47 and test chamber 45 can be separate components attached as described or molded as one unit, and of transparent plastic.

OPERATION

To remove the catheter 40 from container 30 and insert it into the vascular system of a patient, the following is performed. First package 49 can be cut open if desired a tab for it can be provided so that it can be pulled apart, and container 30 removed therefrom. The operator then grasps tab 77 and pulls it upwardly and away from container 30 to remove lid 75 from lip 73 to thus expose catheter connector compartment 34. Then the operator reaches into the connector compartment 72 and grasps the terminals with his phalanges, and a procedure known in the art is followed whereby the various catheter inlet tube terminals are connected, with terminal 312 being first connected to intravenous or pressure tubing (not shown) connected to a saline solution source (not shown) so that the catheter duct connected to terminal 312 is irrigated with saline solution which discharges from the port at 316. The operator can view such discharge into the floor basin 108.

Terminal 310 is also connected to pressure tubing and the catheter duct to which it is connected is irrigated with saline solution which discharges out of the distal tip of the catheter 40 into cavity 47 of test chamber 45. The air initially within cavity 47 is allowed to exit through gas escape conduit 209 so that cavity 47 can be filled to its top. Then terminal 314 is connected to a syringe (not shown) and the syringe is pumped to compress air through the catheter duct connected to terminal 314 to inflate balloon 320 as is known in the art. The operator then views balloon 320 through the transparent chamber 45 to see if there are any air bubbles discharged into the solution within cavity 47, and if no leaks are found, the balloon 320 is deflated.

The thermistor terminal 315 is connected to its electrical unit (not shown) and tested as is known in the art so that it can be insured to give proper temperature readings. If the catheter is one having any additional ducts or functions, they can be tested as is known in the art for satisfactory operation.

If all of the above procedures give positive results, tab 196 is then grasped by the thumb and finger and pulled upwardly, and then pulled above and away from trough 37 in alignment therewith to remove lid 193 from its connection to the trough walls.

Next, the operator's phalanges reach into trough chamber 132 to grasp glove section 255 so as to also grasp catheter 40 within glove section 255, so that the operator can pull catheter 40 towards the proximal end of the trough 37, and by repetitively using short smooth and gentle pulling thrusts, the operator pulls catheter 40 through tube 47. The short strokes are accomplished by pulling the catheter 40 a slight distance then releasing the pleated glove section 255 to allow it to be naturally rebounded by contraction of pleated section 257 towards the distal end of the trough 37, so that the operator can regrasp glove section 255 at its same surface area previously grasped to grasp the catheter 40 within at a more distal position and then pull the catheter 40 back towards the proximal end of trough 37. This procedure is repeated until the distal tip of catheter 40 is located within the catheter guide 271 at a point indicated as "A" in FIG. 1, at which point the catheter 40 recoil size has increased so that catheter 40 abuts container walls 55 and 60 to prevent catheter 40 from being withdrawn any farther into container 40. The size and configuration of walls 55 and 60 prevents removal of catheter 40 out of catheter guide 271 so that guide 271 can function to guide catheter 40 during the process of inserting it into the body.

Next, trough lid 198 is grasped and peeled away from the trough to expose trough recess 169 and trough chamber 154. Container 30 can then be positioned so that the trough passageway 122 is located directly opposite the introducer 276 which has been previously inserted within a vein of the patient as is known in the art. The direction of the potential curve of the distal end of the catheter 40 is directed favorably with respect to the vascular anatomic relationships as is known to one in the art.

The operator then extends his phalanges within trough chambers 132 and 154 to extend along the undersides of glove sections 255 and 259 to simultaneously grasp said sections and lift glove 42 out of trough 37. Glove 42 is pivoted outwardly from container 30 so that the glove sections 251 and 253 are aligned with trough passageway 122, and glove 42 is then moved into passageway 122 so that glove 42 is in the straight horizontal position illustrated as 42' in FIG. 1. Introducer collar 263 and guide 271 are then connected to introducer 276 which has been previously inserted and is indwelling within a vascular structure, as shown in FIGS. 1 and 10.

The less resilient and smaller glove section 255 is then grasped by the operator's phalanges and catheter 40 is gently advanced by small thrusts forward. After each stroke forward, glove 37 is released and the contraction of the more resilient section 253 rebounds less resilient section 255 to its original position so that it can be regrasped to grasp a more proximal part of the catheter 40 within, so that the thrusting stroke can be repeated and the catheter 40 can be cautiously advanced with finger to glove sensitivity into the patient's vein. Thus it can be see that during retraction of catheter 40 from the test chamber 45 or the patient, one of the glove sections of greater resilience acts to rebound the adjacent lesser resilient or nonresilient section back to its original position, while during the insertion of the catheter into the body, the other glove section of greater resilience rebounds the lesser resilient or nonresident section back to its original position from the opposite direction. Thus while it is a function of the sections 253 and 257 of greater resilience to contract or expand to an approximate original position, the smaller sections 251 and 255 do not need to perform that function.

At this stage of the operation, the catheter 40 can be rotated by rotating the container 30, advanced, retracted, irrigated, have its balloon 320 inflated, and have blood drawn from the ports. In addition, the patient can be examined, transported and even resuscitated without disruption of the sterile catheter environment. During the above-described process the glove 42 can be flexed in any direction making the placement of the container 30 with respect to the insertion site less restricted.

After the position of catheter 40 within the patient is considered acceptable by pressure waveform readings, the container 30 can be secured to the patient with tape until X-ray confirmation of the catheter 40 position. If the catheter 40 position is deemed unsatisfactory, the catheter 40 can be withdrawn back into the container 30 by removal thrusts by grasping glove section 255 and applying removal strokes to catheter 40, or can be advanced farther. Alternatively, the patient can be transported to the fluoroscopy room before withdrawal and reinsertion, with the novel device providing a sterile secure environment for the catheter 40 during such transport.

When the operator is satisfied that catheter 40 is in a proper position within the patient, tab 101 is grabbed and lid 100 is peeled away from lips 91 and 97 to expose opening 93. The operator's phalanges then reach through opening 93 and grasp the residual catheter 40 within container 30, and simultaneously the proximal end of glove 42 is grasped near the "O" ring 248 to likewise grasp the washer 231, and the residual catheter 40 is pulled through opening 93, and the washer 231 and its mount plate 228 are pulled upwardly to remove them from container 30. The catheter 40 extending through washer 296 is likewise disengaged from container 30 by pulling it upwardly through washer slit 299, or the catheter 40 and washer 296 can be disengaged from container 30 as a single unit.

To hold the position of catheter 40 relative to washer 231 intact, a strip of bacteria impermeable occlusive tape is wrapped around the washer tapered section 238 and around the portion of catheter 40 adjacent thereto. Other catheter connections desired, dependent on the features of the catheter, can be made as is known in the art. Subsequent manipulation of the catheter 40 while it is indwelling can be accomplished within the sterile confines of the catheter glove 42, the enclosed length of catheter having been never directly exposed to the environment. The glove 42 can be bent to curve in different directions, as the lesser resilient, or nonresilient, glove sections 251 and 255 can be bent or shortened and will not recoil or contract back, which permits the glove 42 to be bent around a portion of the patient's body.

Thus it can be seen that as the various steps are performed, the portions of the catheter 40 which are not being worked with at the time, remain in a sterile compartment protected from contact with surrounding room environment until the time comes for that portion of the catheter 40 to be inserted or attached, and that repetitive complete or partial withdrawal and reinsertion of the catheter 40 is possible without exposure throughout the insertion process until lid 100 is removed, and that partial insertion or withdrawal of the gloved catheter which has never been directly exposed to the environment remains possible throughout the indwelling period after insertion.

Turning now to the modification of FIGS. 15 and 16, there is shown a modification which is particularly suited for accommodating catheters of longer than standard length, and which illustrates a container 30" of generally more compact structure than the container 30. Container 30" similarly has a main housing compartment 32", a catheter connector compartment 34", a trough 37", a pleated tubular glove 42", a spherical test chamber 45", a tube 47" connecting chamber 45" to trough 37". The structure of the embodiment of FIGS. 15 and 16 is similar to that of the earlier discussed embodiment and the drawings have been numbered to show for example a roof 80" for the main housing compartment, a lip 91" for the opening of the main housing compartment, an opening 93" for the main housing compartment, and a lid 100" to cover said opening. The catheter, 40", coils twice within the main housing compartment with a smaller loop and a larger loop, with the larger loop abutting the exterior wall 55" of the main compartment 32, and with the smaller coil spaced apart from wall 55".

It can be seen that the catheter connector compartment 34" has a shape that differs from that of its related compartment 34, although the function is the same, and the connector compartment similarly houses the various catheter terminals. Other parts of the embodiment of FIGS. 15 and 16 have been numbered for reference with double prime indications being used.

FIG. 16 shows a modification with a lid 75" covering compartment 34" and a modification of the wall structure for compartment 34". The walls forming the connector compartment, 60", 62", 70", and 67" are structured so that wall 67" is taller than the other walls, with walls 65" and 70" slanting downward away from wall 67", and with the lid 75" extending over the lip 73" formed about the walls being slanted. This permits the lid 75" to overlie a portion of the lid 100" so that the angle of juncture of those two lids is about 10°, much less than a right-angular junction, which permits the adhesive on lid 75" to attach better to the top of lid 100" than in the embodiment of FIG. 1 although sufficient adhesive can be provided with the FIG. 1 embodiment to provide a secure seal.

With the FIGS. 15 and 16 embodiment, when the distal tip of the catheter 40" is withdrawn into the catheter guide tube a pre-determined distance, the inner coil of the catheter 40" also abuts the container wall 55" to prevent the distal tip of the catheter 40" to be withdrawn farther away from the test cavity. The various lids for the compartments can be removed and the same procedure followed as explained for the FIG. 1 embodiment.

This modification further has a bidirectional rotatable bumper tube 350 which is telescopically and rotatably mounted about a bumper cylinder 103" which is integral with the floor 52", just as bumper cylinder 103 is integral with floor 52. Bumper tube 350 is not attached to lid 100" and freely rotates when the smaller loop of catheter 40" contracts around it so that catheter 40" can be more easily additional advanced by contraction of the larger loop of catheter 40".

FIGS. 17 and 18 show another embodiment in which the catheter 40''' is shown housed in a container 30''', with other container components being numbered with triple prime indications as done for the FIGS. 15 and 16 embodiment to correspond to components shown in the FIG. 1 embodiment. In this embodiment, the container 30''' has a bulging section 400 having a curved wall 402 offshooting from the wall 55''' of main compartment 32'''. In this embodiment a substantial portion of the catheter 40''' initially abuts the wall 55''', with such abutment acting to resist jarring movement of the catheter 40''' within the container 30''' during shipment and movement of the container 30'''. The bulging section 400 is located to extend beneath the catheter connector compartment 34''' so that the roof 80''' of the main housing compartment 32''' forms a part of the floor of the connector compartment 34'''. The connector compartment 34''' is of different shape than the embodiment of FIG. 1, but performs the same function and has a lid 75''' sealing to the lip 73''' to cover the opening of the connector compartment, with the tab 77''' for removing lid 75''' being located at the other end of the container 30'''. When the distal tip of catheter 40''' is withdrawn into the guide tube a predetermined distance, the catheter 40''' extends into the bulging section 400 to abut the wall 402 of section 400 to prevent the distal tip of catheter 40''' from being withdrawn farther from the cavity of test chamber 45'''. The procedure of exposing the various container compartments is the same as that previously described for the FIG. 1 embodiment.

What is claimed is:

1. An intravascular catheter preparation and dispensing container comprising:
   (a) a main housing compartment for housing a coiled portion of an intravascular catheter, said housing having an opening for removal of the catheter therethrough;
   (b) means for covering the main housing compartment opening to seal the housing compartment from microorganisms and particles in the surrounding environment but removable from said main housing compartment to expose the housing opening;
   (c) a catheter connector compartment for housing a more proximal portion of the catheter, said connector compartment having an opening for removal of the catheter portion within; and
   (d) means for covering the connector compartment opening to seal the connector compartment from bacteria and particles in the surrounding environment but removable from the connector compartment to expose the connector compartment opening.

2. The structure of claim 1, further comprising:
   (a) a trough compartment for housing a more distal portion of the catheter, said trough having an opening for removal of a portion of the catheter therethrough; and
   (b) means for covering the trough to seal its interior from microorganisms particles in the surrounding environment but removable from the trough to expose at least a portion of the trough's interior.

3. The structure of claim 2 wherein the trough has an upwardly slant relative to the main housing compartment.

4. The structure of claim 2 wherein the trough has an interior portion sized to receive the phalanges, and the means for covering the trough comprises at least one lid detachably connected to the trough and removable by hand to expose said trough interior portion to permit the phalanges to reach inside the trough.

5. The structure of claim 4 further comprising the trough having at least two interior portions sized to allow insertion of the phalanges therein, and a second lid detachably mounted to the trough and removable by hand so that upon removal of both trough lids both of said trough interior portions are exposed to permit insertion of the phalanges therein.

6. The structure of claim 4 wherein the trough has a passageway extending therethrough for allowing a portion of the catheter to be lifted out of the trough and laid to pass through the passageway for facilitating insertion of the catheter within a patient's body.

7. The structure of claim 1 further comprising a test chamber with a cavity for receiving the distal catheter end and a flotation balloon mounted to the distal catheter end, with means for connecting the test chamber to other container structure to prevent catheter exposure to the environment outside the container.

8. The structure of claim 7 wherein the means for connecting the test chamber comprises a tube through which the catheter can slide.

9. The structure of claim 8 wherein the tube has a principal conduit for allowing passage of the catheter therethrough, and a second gas escape conduit in fluid connection with the top of the test chamber cavity, and in connection with the main tube conduit to permit gas within the test cavity to flow from the test cavity into the principal tube conduit.

10. The structure of claim 9 wherein the test chamber is transparent and is mounted above the main housing compartment.

11. The structure of claim 7 wherein the relationship between the structure forming the main housing compartment and the catheter length is such to provide means so that when the catheter is moved a predetermined distance out of the test chamber cavity, a portion of the catheter located within the main compartment abuts structure of the main compartment so that the catheter cannot be withdrawn farther away from the test cavity.

12. The structure of claim 11 wherein the main housing compartment further comprises a bulging section and wherein the main compartment is sized so that a catheter of predetermined length can be housed within to abut a portion of a structure forming the main compartment, and so that when the catheter is withdrawn from the test cavity a predetermined distance, a portion of the catheter is moved into the bulging section to abut the structure forming the bulging section to prevent further withdrawal of the catheter away from the test cavity.

13. The structure of claim 12 wherein the main compartment can house a multiple looped portion of a catheter of predetermined length with a portion of a larger loop housed therein initially abutting a portion of the structure forming the main compartment, and with a smaller inner loop so that when the catheter is withdrawn a predetermined distance away from the test cavity, a part of the inner loop expands to abut a portion of the main compartment structure to prevent further removal of the catheter away from the test cavity.

14. The structure of claim 2 further comprising a tubular glove surrounding a more distal segment of the catheter, and having proximal and distal ends each with means to be connected about the catheter so that the catheter can slide through the glove, the glove being housed within the trough, and the glove having resilient means for allowing the phalanges to grasp about it and slide the catheter therethrough and to allow the glove to contract and expand along the catheter.

15. The structure of claim 14 wherein the trough has a portion sized to allow insertion of the phalanges to grasp the glove and remove the glove and catheter segment within the glove from the trough.

16. The structure of claim 15 wherein the glove has a guide tube at its distal end to receive and guide passage of the catheter therethrough.

17. The structure of claim 16 wherein the glove is transparent.

18. The structure of claim 15 wherein the distal glove end is connected to a collar, and the collar has a catheter guide tube mounted therein so that the catheter can pass through the guide tube and collar, and with the trough having a recessed area to house the collar and be covered by the means for sealing the trough.

19. The structure of claim 15 wherein the glove has a first section of greater resilience and a second section of lesser resilience for grasping by the hand.

20. The structure of claim 19 further comprising the glove having a third section of greater resilience, with the second section of lesser resilience interspaced between the first and third sections of greater resilience, so that when the second section is grasped and moved in a first direction and then released, the first section of greater resilience acts to contract and return the second section back towards the first section, and when the second section is moved in the opposite direction, the third section acts to contract to return the second section back towards the third section.

21. The structure of claim 19 wherein the first section of greater resilience is pleated.

22. The structure of claim 20 wherein the first and third sections of greater resilience are pleated.

23. The structure of claim 22 wherein the second section is pleated and has pleats of smaller diameter than the pleats of the first and third sections.

24. The structure of claim 14 wherein the proximal end of the glove has a washer with a distal bore section which decreases in size from the distal end of the washer towards the proximal end of the washer.

25. The structure of claim 24 wherein the washer has a proximal exterior tapered end for allowing tape to be wrapped around it and the catheter after the catheter is inserted a desired position within the patient and is removed from the container.

26. The structure of claim 4 wherein the main housing section has a bumper about which the catheter can be initially coiled, and wherein the housing compartment has a floor with a basin associated therewith for receiving liquid emitting from a catheter duct port during initial flushing of said duct.

27. The structure of claim 2 wherein the main housing section has a bumper rotatably mounted thereto, with the catheter coiled about the bumper, so that the bumper rotates when the catheter frictionally engages the bumper and is pulled around it.

28. The structure of claim 1 further comprising a washer mounted between the main compartment and the connector compartment and having an opening therethrough for passage of the catheter from the connector compartment to the main compartment, the washer having an upwardly extending slit for pulling of the catheter therethrough.

29. The structure of claim 1 further comprising a package for housing the container.

30. An intravascular catheter glove of tubular shape for surrounding a portion of a catheter, the glove having distal and proximal ends each with means to be tightly connected about the catheter but which allow the catheter to slide therethrough, the glove having a first section of greater resilience and a second section at lesser resilience.

31. The structure of claim 30 further comprising the glove having a third section of greater resilience, with the second section of lesser resilience interspaced between the first and third sections of greater resilience, so that when the second section is grasped and moved in a first direction and then released, the first section of greater resilience acts to contract and return the second section back towards the first section and when the second section is moved in the opposite direction, the third section acts to contract to return the second section back towards the third section.

32. The structure of claim 30 wherein the first section of greater resilience is pleated.

33. The structure of claim 31 wherein the first and third sections of greater resilience are pleated.

34. The structure of claim 33 wherein the second section is pleated and has pleats of smaller diameter than those of the first and third sections.

35. The structure of claim 30 further comprising a catheter guide tube mounted near the distal end of the glove to receive and guide passage of the catheter therethrough.

36. An intravascular preparation and dispensing container comprising:
(a) a main housing compartment for housing a coiled portion of a catheter, said housing having an opening for removal of the catheter therethrough;
(b) means for sealing the housing opening; and
(c) a test chamber with a cavity for receiving the distal catheter end and a flotation balloon mounted to the distal catheter end, with means connecting the test chamber to other container structures to prevent catheter exposure to the environment outside the container.

37. An intravascular catheter preparation and dispensing container comprising:
(a) a main housing compartment for housing a coiled portion of an intravascular catheter, said housing compartment having an opening to permit the phalanges to extend therethrough and grasp a portion of the coiled catheter within and pull it through said opening;
(b) a first lid with means for being detachably secured to the container to seal the housing opening from bacteria and particulate matter but removable by the phalanges to expose the housing opening for catheter removal;
(c) a catheter connector compartment for containing a proximal portion of the catheter, said connector compartment having an opening to allow insertion of the phalanges therein for grasping the catheter portion contained within and removing it therefrom;
(d) a second lid with means for being detachably secured to the container to seal the connector compartment opening from microorganisms and particulate matter but removable by the hand to expose the connector compartment opening for removal of the catheter portion within;
(e) a tubular glove surrounding a more distal catheter segment and having proximal and distal ends connected about the catheter so that the catheter can slide through the glove, the glove having means for allowing the phalanges to grasp about it and slide the catheter therethrough and to allow the glove to contract and expand along the catheter;
(f) a trough with means for being connected to the main compartment to permit the catheter to pass from the main compartment into the trough, the trough being sized to house the glove, and having one chamber of sufficient size to allow insertion of the phalanges about the glove and removal of the glove therefrom by the phalanges;
(g) means for sealing the trough interior from microorganisms and particulate matter, but detachable by hand to expose the trough for grasping and removal of the glove and catheter portion within;
(h) a transparent test chamber having a cavity which receives the distal end of the catheter and a flotation balloon mounted to the distal catheter end, the test cavity sized to allow the balloon to inflate to normal size within so that when the test cavity is filled with liquid and the balloon inflated with gas, the gas can bubble through any balloon leaks into the cavity for detection by an observer; and
(i) means for enclosing the catheter from its position in the test cavity to its position within the trough to permit protected passage of the catheter from the test cavity to the trough.

38. The structure of claim 37 wherein the means for enclosing the catheter from the test cavity to the trough is a tube with a first conduit for passage of the catheter therethrough and a second gas escape conduit in fluid connection with the top of the test cavity and in fluid connection with the first tube conduit to allow gas initially within the test cavity to escape therethrough when the test cavity is filled with liquid from the catheter, and to allow leakage gas from the balloon to escape therethrough.

39. The structure of claim 38 wherein the proximal end of the gas escape conduit is in fluid connection with the highest point of the first tube conduit.

40. An intravascular catheter preparation and dispensing container comprising:
(a) a main housing compartment for housing a coiled portion of an intravascular catheter, said housing compartment having an opening to permit the phalanges to extend therethrough and grasp a portion of the coiled catheter within and pull it through said opening;
(b) a first lid with means for being detachably secured to the container to seal the main housing opening from microorganisms and particulate matter but removable by the hand to expose the housing opening for catheter removal, at least a portion of the structure of the first lid and main housing compartment being transparent to permit viewing of the catheter within the main compartment;
(c) a catheter connector compartment adjacent the main housing compartment for containing a proximal portion of the catheter including catheter terminals, said connector compartment having an opening to allow insertion of the phalanges therein for grasping the catheter portion within and removing it therefrom;
(d) a second lid with means for being detachably secured to the container to seal the connector compartment opening from microorganisms and particulate matter but removable by the hand to expose the connector compartment opening for removal of the catheter portion within at least a portion of the structure of the second lid and connector compartment being transparent to permit viewing of the catheter within the connector compartment;

(e) a tubular glove surrounding a more distal catheter segment and having proximal and distal ends connected about the catheter so that the catheter can slide through the glove, the glove having means for allowing the phalanges to grasp about it and slide the catheter therethrough and to allow the glove to contract and expand along the catheter, with a guide tube mounted by a collar to the distal glove end to allow passage of the catheter therethrough and to guide the catheter;

(f) a trough with means for being connected to the main compartment to permit the catheter to pass from the main compartment into the trough, the trough being sized to house the glove, and having a chamber of sufficient size to allow insertion of the phalanges about the glove and removal of the glove therefrom by the phalanges;

(g) means for sealing the trough interior from microorganisms and particulate matter but detachable by hand to expose the trough for grasping and removal of the glove and catheter portion within;

(h) a transparent test chamber having a cavity to receive the distal catheter end and a flotation balloon mounted to the distal catheter end, the test cavity sized to allow the balloon to inflate to normal size within so that when the test cavity is filled with liquid and the balloon inflated with gas, the gas can bubble through any balloon leaks into the cavity for detection by an observer; and (i) a tube connecting the test cavity to the trough with a first conduit for passage of the catheter therethrough, and a second gas escape conduit in fluid connection with the top of the test cavity and in fluid connection with the highest point of the first tube conduit to allow gas initially within the test cavity to escape therethrough when the test cavity is filled with liquid from the catheter, and to allow leakage gas from the balloon to escape therethrough; and (j) structural means for providing the relationship between the structure forming the main compartment and the catheter length to be such so that when the catheter is moved a predetermined distance out of the test chamber cavity so that the distal tip of the catheter is within the guide tube, a portion of the catheter located within the main compartment abuts the structure of the main compartment to prevent the catheter to be withdrawn farther away from the test cavity and out of the guide tube.

41. The structure of claim 40 further comprising means for allowing gas to pass through part of the container structure into the interior of the container to permit gas sterilization of the interior of the container.

42. An intravascular preparation and dispensing container for a catheter comprising:

(a) a main housing compartment for housing a coiled portion of the catheter, the said housing having an opening for removal of the catheter therethrough;

(b) means for sealing the housing opening; and (c) a test chamber with a cavity for receiving a portion of the catheter, the test chamber being constucted so that the cavity can be filled with liquid and hold the liquid within the cavity, with means connecting the test chamber to other container structure to prevent catheter exposure to the environment outside the container.

43. The structure of claim 42 wherein the test chamber has means for permitting one viewing the chamber from the exterior thereof to see the catheter portion inside the cavity.

44. The structure of claim 43 wherein the test cavity is sized to allow a balloon connected to the catheter portion to inflate to normal size within so that when the test cavity is filled with liquid and the balloon inflated with gas, gas bubbling through any balloon leaks into the cavity can be detected by an observer.

45. The structure of claim 44 wherein the test chamber comprises transparent material for permitting viewing therethrough to see the interior of the cavity.

46. The structure of claim 42 wherein the means for connecting the test chamber comprises a tube through which the catheter can slide.

47. The structure of claim 42 wherein in the preamble the catheter has a duct and wherein the test chamber is positioned to be in fluid communication with the catheter duct so that fluid injected through said catheter duct can enter the test chamber and can be retained within the test chamber.

48. The structure of claim 47 wherein the test chamber comprises a transparent portion to permit viewing therethrough to see the interior of the cavity.

49. The structure of claim 42 wherein the relationship between the structure forming the main housing compartment and the catheter length is such to provide means so that when the catheter is moved a predetermined distance out of the test chamber cavity, a portion of the catheter located within the main compartment abuts structure of the main compartment so that the catheter cannot be withdrawn farther away from the test cavity.

50. An intravascular catheter preparation and dispensing container comprising:

(a) a main housing compartment for housing a coiled portion of an intravascular catheter, said housing having an opening for removal of the catheter therethrough;

(b) means for covering the main housing compartment opening to seal the housing compartment from microorganisms and particles in the surrounding environment but removable from said main housing compartment to expose the housing opening;

(c) a trough compartment for housing a more distal portion of the catheter, said trough having an opening for removal of a portion of the catheter therethrough;

(d) means for covering the trough to seal its interior from microorganism particles in the surrounding environment but removable from the trough to expose at least a portion of the trough's interior; and (e) a tubular glove surrounding a more distal segment of the catheter, and having proximal and distal ends each with means to be connected about the catheter so that the catheter can slide through the glove, the glove being housed within the trough, and the glove having resilient means for allowing the phalanges to grasp about it and slide the catheter therethrough and to allow the glove to contract and expand along the catheter.

51. The structure of claim 50 further comprising means for mounting the distal end of the tubular glove to the container against movement by forces normally applied to the glove to slide the catheter through the glove, but permitting removal of the distal catheter end by application of force in a preselected direction, and means for removably mounting the proximal end of the tubular glove to the trough against forces normally applied to the glove to slide the catheter through the glove but permitting removal of the proximal glove end by application of force in a preselected direction.

52. The structure of claim 51 wherein the means for covering the main housing compartment has means for mounting the proximal end of the glove against removal from the container but permitting removal of the proximal glove end from the container when the means for covering the main housing is at least partially removed from the container.

53. The structure of claim 51 wherein the means for covering the trough has means for mounting the distal end of the glove against removal from the trough but permitting removal of the distal glove end from the trough when the means for covering the trough is at least partially removed from the trough.

54. The structure of claim 51 wherein the trough has a portion size to allow insertion of the phalanges to grasp the glove and remove the glove and catheter segment within the glove from the trough.

55. The structure of claim 54 wherein the glove has a guide tube at its distal end to receive and guide passage of the catheter therethrough.

56. The structure of claim 55 wherein the glove is transparent.

57. The structure of claim 53 wherein the distal glove end is connected to a collar, and the collar has a catheter guide tube mounted therein so that the catheter can pass through the guide tube and collar, and further with the trough having a recessed area to house the collar and be covered by the means for sealing the trough.

58. The structure of claim 14 further comprising means for mounting the distal end of the tubular glove to the container against movement by forces normally applied to the glove to slide the catheter through the glove, but permitting removal of the distal catheter end by application of force in a preselected direction, and means for removably mounting the proximal end of the tubular glove to the trough against forces normally applied to the glove to slide the catheter through the glove but permitting removal of the proximal glove end by application of force in a preselected direction.

59. An intravascular catheter preparation and dispensing container assembly comprising:
(a) an intravascular catheter, the said catheter being capable of being coiled and having a coiled portion;
(b) a main housing compartment for housing the coiled portion of the catheter, said housing having an opening for removal of the catheter therethrough;
(c) means for covering the main housing compartment opening to seal the housing compartment from microorganisms and particles in the surrounding environment but removable from said housing compartment to expose the housing opening;
(d) a catheter connector compartment for housing a more proximal portion of the catheter, said connector compartment having an opening for removal of the catheter portion within; and
(e) means for covering the connector compartment opening to seal the connector compartment from bacteria and particles in the surrounding environment but removable from the connector compartment to expose the connector compartment opening.

60. The structure of claim 59, further comprising:
(a) a trough compartment for housing a more distal portion of the catheter, said trough having an opening for removal of a portion of the catheter therethrough; and
(b) means for covering the trough to seal its interior from microorganisms particles in the surrounding environment but removable from the trough to expose at least a portion of the trough's interior.

61. The structure of claim 60 wherein the trough has an upwardly slant relative to the main housing compartment.

62. The structure of claim 60 wherein the trough has an interior portion sized to receive the phalanges, and the means for covering the trough comprises at least one lid detachably connected to the trough and removable by hand to expose said trough interior portion to permit the phalanges to reach inside the trough.

63. The structure of claim 62 further comprising the trough having at least two interior portions sized to allow insertion of the phalanges therein, and a second lid detachably mounted to the trough and removable by hand so that upon removal of both trough lids both of said trough interior portions are exposed to permit insertion of the phalanges therein.

64. The structure of claim 62 wherein the trough has a passageway extending therethrough for allowing a portion of the catheter to be lifted out of the trough and laid to pass through the passageway for facilitating insertion of the catheter within a patient's body.

65. The structure of claim 59 further comprising a test chamber with a cavity for receiving the distal catheter end and a flotation balloon mounted to the distal catheter end, with means for connecting the test chamber to other container structure to prevent catheter exposure to the environment outside the container.

66. The structure of claim 65 wherein the means for connecting the test chamber comprises a tube through which the catheter can slide.

67. The structure of claim 66 wherein the tube has a principal conduit for allowing passage of the catheter therethrough, and a second gas escape conduit in fluid connection with the top of the test chamber cavity, and in connection with the main tube conduit to permit gas within the test cavity to flow from the test cavity into the principal tube conduit.

68. The structure of claim 67 wherein the test chamber is transparent and is mounted above the main housing compartment.

69. The structure of claim 65 wherein the relationship between the structure forming the main housing compartment and the catheter length is such to provide means so that when the catheter is moved a predetermined distance out of the test chamber cavity, a portion of the catheter located within the main compartment abuts structure of the main compartment so that the catheter cannot be withdrawn farther away from the test cavity.

70. The structure of claim 69 wherein the catheter is of a predetermined length and the main housing compartment further comprises a bulging section and wherein the main compartment is sized so that the catheter of predetermined length can be housed within to abut a portion of a structure forming the main compartment, and so that when the catheter is withdrawn from the test cavity a predetermined distance, a portion of the catheter is moved into the bulging section to abut the structure forming the bulging section to prevent further withdrawal of the catheter away from the test cavity.

71. The structure of claim 70 wherein the catheter is of a predetermined length and the main compartment can house a multiple looped portion of the catheter of predetermined length with a portion of a larger loop housed therein initially abutting a portion of the structure forming the main compartment, and with a smaller inner loop so that when the catheter is withdrawn a predetermined distance away from the test cavity, a part of the inner loop expands to abut a portion of the main compartment structure to prevent further removal of the catheter away from the test cavity.

72. The structure of claim 60 further comprising a tubular glove surrounding a more distal segment of the catheter, and having proximal and distal ends each with means to be connected about the catheter so that the catheter can slide through the glove, the glove being housed within the trough, and the glove having resilient means for allowing the phalanges to grasp about it and slide the catheter therethrough and to allow the glove to contract and expand along the catheter.

73. The structure of claim 71 wherein the trough has a portion sized to allow insertion of the phalanges to grasp the glove and remove the glove and catheter segment within the glove from the trough.

74. The structure of claim 73 wherein the glove has a guide tube at its distal end to receive and guide passage of the catheter therethrough.

75. The structure of claim 74 wherein the glove is transparent.

76. The structure of claim 23 wherein the distal glove end is connected to a collar, and the collar has a catheter guide tube mounted therein so that the catheter can pass through the guide tube and collar, and with the trough having a recessed area to house the collar and be covered by the means for sealing the trough.

77. The structure of claim 73 wherein the glove has a first section of greater resilience and a second section of lesser resilience for grasping by the hand.

78. The structure of claim 77 further comprising the glove having a third section of greater resilience, with the second section of lesser resilience interspaced between the first and third sections of greater resilience, so that when the second section is grasped and moved in a first direction and then released, the first section of greater resilience acts to contract and return the second section back towards the first section, and when the second section is moved in the opposite direction, the third section acts to contract to return the second section back towards the third section.

79. The structure of claim 77 wherein the first section of greater resilience is pleated.

80. The structure of claim 78 wherein the first and third sections of greater resilience are pleated.

81. The structure of claim 80 wherein the second section is pleated and has pleats of smaller diameter than the pleats of the first and third sections.

82. The structure of claim 72 wherein the proximal end of the glove has a washer with a distal bore section which decreases in size from the distal end of the washer towards the proximal end of the washer.

83. The structure of claim 72 wherein the washer has a proximal exterior tapered end for allowing tape to be wrapped around it and the catheter after the catheter is inserted a desired position within the patient and is removed from the container.

84. The structure of claim 62 wherein the main housing section has a bumper about which the catheter can be initially coiled, and wherein the housing compartment has a floor with a basin associated therewith for receiving liquid emitting from a catheter duct port during initial flushing of said duct.

85. The structure of claim 60 wherein the main housing section has a bumper rotatably mounted thereto, with the catheter coiled about the bumper, so that the bumper rotates when the catheter frictionally engages the bumper and is pulled around it.

86. The structure of claim 59 further comprising a washer mounted between the main compartment and the connector compartment and having an opening therethrough for passage of the catheter from the connector compartment to the main compartment, the washer having an upwardly extending slit for pulling of the catheter therethrough.

87. The structure of claim 59 further comprising a package for housing the container.

88. An intravascular preparation and dispensing container assembly comprising:
(a) an intravascular catheter having a distal end, the said catheter being capable of being coiled and having a coiled portion, the catheter having a balloon mounted near the distal catheter end;
(b) a main housing compartment for housing the coiled portion of the catheter, said housing having an opening for removal of the catheter therethrough;
(c) means for sealing the housing opening; and
(d) a test chamber with a cavity for receiving the distal catheter end and the flotation balloon, with means connecting the test chamber to other container structures to prevent catheter exposure to the environment outside the container.

89. An intravascular catheter preparation and dispensing container assembly comprising:
(a) an intravascular catheter, the said catheter being capable of being coiled and having a coiled portion, the catheter having a distal end with a flotation balloon mounted near the distal end;
(b) a main housing compartment for housing the coiled portion of the catheter, said housing compartment having an opening to permit the phalanges to extend therethrough and grasp a portion of the coiled catheter within and pull it through said opening;
(c) a first lid with means for being detachably secured to the container to seal the housing opening from bacteria and particulate matter but removable by the phalanges to expose the housing opening for catheter removal;
(d) a catheter connector compartment for containing a proximal portion of the catheter, said connector compartment having an opening to allow insertion of the phalanges therein for grasping the catheter portion contained within and removing it therefrom;

(e) a second lid with means for being detachably secured to the container to seal the connector compartment opening from microorganisms and particulate matter but removable by the hand to expose the connector compartment opening for removal of the catheter portion within;

(f) a tubular glove surrounding a more distal catheter segment and having proximal and distal ends connected about the catheter so that the catheter can slide through the glove, the glove having means for allowing the phalanges to grasp about it and slide the catheter therethrough and to allow the glove to contract and expand along the catheter;

(g) a trough with means for being connected to the main compartment to permit the catheter to pass from the main compartment into the trough, the trough being sized to house the glove, and having one chamber of sufficient size to allow insertion of the phalanges about the glove and removal of the glove therefrom by the phalanges;

(h) means for sealing the trough interior from microorganisms and particulate matter, but detachable by hand to expose the trough for grasping and removal of the glove and catheter portion within;

(i) a transparent test chamber having a cavity which receives the distal catheter end and the flotation balloon, the test cavity sized to allow the balloon to inflate to normal size within so that when the test cavity is filled with liquid and the balloon inflated with gas, the gas can bubble through any balloon leaks into the cavity for detection by an observer; and (j) means for enclosing the catheter from its position in the test cavity to its position within the trough to permit protected passage of the catheter from the test cavity to the trough.

90. The structure of claim 37 wherein the means for enclosing the catheter from the test cavity to the trough is a tube with a first conduit for passage of the catheter therethrough and a second gas escape conduit in fluid connection with the top of the test cavity and in fluid connection with the first tube conduit to allow gas initially within the test cavity to escape therethrough when the test cavity is filled with liquid from the catheter, and to allow leakage gas from the balloon to escape therethrough.

91. The structure of claim 90 wherein the proximal end of the gas escape conduit is in fluid connection with the highest point of the first tube conduit.

92. An intravascular catheter preparation and dispensing container comprising:

(a) an intravascular catheter, the said catheter being capable of being coiled and having a coiled portion, the catheter having a distal end with a flotation balloon mounted near the distal end, the catheter having a proximal portion with terminals;

(b) a main housing compartment for housing the coiled portion of the intravascular catheter, said housing compartment having an opening to permit the phalanges to extend therethrough and grasp a portion of the coiled catheter within and pull it through said opening;

(c) a first lid with means for being detachably secured to the container to seal the main housing opening from microorganisms and particulate matter but removable by the hand to expose the housing opening for catheter removal, at least a portion of the structure of the first lid and main housing compartment being transparent to permit viewing of the catheter within the main compartment;

(d) a catheter connector compartment adjacent the main housing compartment for containing the proximal portion of the catheter including the terminals, said connector compartment having an opening to allow insertion of the phalanges therein for grasping the catheter portion within and removing it therefrom;

(e) a second lid with means for being detachably secured to the container to seal the connector compartment opening from microorganisms and particulate matter but removable by the hand to expose the connector compartment opening for removal of the catheter portion within at least a portion of the structure of the second lid and connector compartment being transparent to permit viewing of the catheter within the connector compartment;

(f) a tubular glove surrounding a more distal catheter segment and having proximal and distal ends connected about the catheter so that the catheter can slide through the glove, the glove having means for allowing the phalanges to grasp about it and slide the catheter therethrough and to allow the glove to contract and expand along the catheter, with a guide tube mounted by a collar to the distal glove end to allow passage of the catheter therethrough and to guide the catheter;

(g) a trough with means for being connected to the main compartment to permit the catheter to pass from the main compartment into the trough, the trough being sized to house the glove, and having a chamber of sufficient size to allow insertion of the phalanges about the glove and removal of the glove therefrom by the phalanges;

(h) means for sealing the trough interior from microorganisms and particulate matter but detachable by hand to expose the trough for grasping and removal of the glove and catheter portion within;

(i) a transparent test chamber having a cavity to receive the distal catheter end and flotation balloon, the test cavity sized to allow the balloon to inflate to normal size within so that when the test cavity is filled with liquid and the balloon inflated with gas, the gas can bubble through any balloon leaks into the cavity for detection by an observer;

(j) a tube connecting the test cavity to the trough with a first conduit for passage of the catheter therethrough, and a second gas escape conduit in fluid connection with the top of the test cavity and in fluid connection with the highest point of the first tube conduit to allow gas initially within the test cavity to escape therethrough when the test cavity is filled with liquid from the catheter, and to allow leakage gas from the balloon to escape therethrough; and (k) structural means for providing the relationship between the structure forming the main compartment and the catheter length to be such so that when the catheter is moved a predetermined distance out of the test chamber cavity so that the distal tip of the catheter is within the guide tube, a portion of the catheter located within the main compartment abuts the structure of the main compartment to prevent the catheter to be withdrawn farther away from the test cavity and out of the guide tube.

93. The structure of claim 92 further comprising means for allowing gas to pass through part of the container structure into the interior of the container to permit gas sterilization of the interior of the container.

94. An intravascular preparation and dispensing container assembly comprising:
(a) an intravascular catheter being capable of being coiled and having a coiled portion;
(b) a main housing compartment for housing the coiled portion of the catheter, the said housing having an opening for removal of the catheter therethrough;
(c) means for sealing the housing opening; and
(d) a test chamber with a cavity for receiving a portion of the catheter, the test chamber being constructed so that the cavity can be filled with liquid and hold the liquid within the cavity, with means connecting the test chamber to other container structure to prevent catheter exposure to the environment outside the container.

95. The structure of claim 94 wherein the test chamber has means for permitting one viewing the chamber from the exterior thereof to see the catheter portion inside the cavity, the test cavity being sized to allow a balloon connected to the catheter portion to inflate to normal size within so that when the test cavity is filled with liquid and the balloon inflated with gas, gas bubbling through any balloon leaks into the cavity can be detected by an observer.

* * * * *